(12) United States Patent
Huang et al.

(10) Patent No.: US 9,850,190 B2
(45) Date of Patent: Dec. 26, 2017

(54) PROCESS FOR PREPARING DICHLOROPROPANOL

(71) Applicant: CHANG CHUN PLASTICS CO., LTD., Taipei (TW)

(72) Inventors: Chien-Fu Huang, Taipei (TW); Cheng-Hui Chan, Taipei (TW)

(73) Assignee: Chang Chun Plastics Co., Ltd., Taipei (TW)

( * ) Notice: Subject to any disclaimer, the term of this patent is extended or adjusted under 35 U.S.C. 154(b) by 0 days.

(21) Appl. No.: 15/263,727

(22) Filed: Sep. 13, 2016

(65) Prior Publication Data

US 2017/0174593 A1    Jun. 22, 2017

(30) Foreign Application Priority Data

Dec. 18, 2015 (TW) ............................ 104142675 A

(51) Int. Cl.
C07C 31/34 (2006.01)
C07C 29/62 (2006.01)
C07C 29/80 (2006.01)
C07C 29/86 (2006.01)

(52) U.S. Cl.
CPC .............. *C07C 29/62* (2013.01); *C07C 29/80* (2013.01); *C07C 29/86* (2013.01)

(58) Field of Classification Search
None
See application file for complete search history.

(56) References Cited

U.S. PATENT DOCUMENTS

| | | | |
|---|---|---|---|
| 2,144,612 A | 1/1939 | Britton et al. | |
| 2,198,600 A | 4/1940 | Britton et al. | |
| 2,279,509 A | 4/1942 | Britton et al. | |
| 3,954,874 A | 5/1976 | Christidis | |
| 4,714,604 A * | 12/1987 | Olson | C01B 7/0706 203/50 |
| 4,973,763 A | 11/1990 | Jakobson et al. | |

FOREIGN PATENT DOCUMENTS

| | | |
|---|---|---|
| CN | 1845888 | 10/2006 |
| CN | 101134714 | 3/2008 |
| CN | 101456793 A * | 6/2009 |
| CN | 100509726 | 7/2009 |
| CN | 100519497 | 7/2009 |
| CN | 101531442 | 9/2009 |
| CN | 101031532 | 11/2010 |
| CN | 102010295 | 4/2011 |
| CN | 101429099 | 12/2011 |
| CN | 101774886 | 10/2013 |
| CN | 102675047 | 8/2014 |
| JP | 2008507526 | 3/2008 |
| JP | 2010523703 | 7/2010 |
| JP | 2012513983 | 6/2012 |
| TW | 200510284 | 3/2005 |
| TW | 200533638 | 10/2005 |
| TW | 200613254 | 5/2006 |
| TW | 200642999 | 12/2006 |
| TW | 200700359 | 1/2007 |
| TW | 200700360 | 1/2007 |
| TW | 200700361 | 1/2007 |
| TW | 200700362 | 1/2007 |
| TW | 200700363 | 1/2007 |
| TW | 200700364 | 1/2007 |
| TW | 200700365 | 1/2007 |
| TW | 200700366 | 1/2007 |
| TW | 200700367 | 1/2007 |
| TW | 200700401 | 1/2007 |
| TW | 200700402 | 1/2007 |
| TW | 200700403 | 1/2007 |
| TW | 200714577 | 4/2007 |
| TW | 200902488 | 1/2009 |
| TW | 200918493 | 5/2009 |
| TW | 200942525 | 10/2009 |
| TW | I339654 | 4/2011 |
| WO | 2005021476 | 3/2005 |
| WO | 2005054167 | 6/2005 |
| WO | 2006020234 | 2/2006 |
| WO | 2006100312 | 9/2006 |
| WO | 2006100313 | 9/2006 |
| WO | 2006100314 | 9/2006 |
| WO | 2006100315 | 9/2006 |
| WO | 2006100316 | 9/2006 |
| WO | 2006100317 | 9/2006 |
| WO | 2006100318 | 9/2006 |
| WO | 2006100319 | 9/2006 |
| WO | 2006100320 | 9/2006 |
| WO | 2006106153 | 10/2006 |
| WO | 2006106154 | 10/2006 |
| WO | 2006111810 | 10/2006 |
| WO | 2007054505 | 5/2007 |
| WO | 2009066327 | 5/2009 |
| WO | 2014049625 | 4/2014 |

OTHER PUBLICATIONS

Machine translation of CN 101456793A.*

* cited by examiner

*Primary Examiner* — Sudhakar Katakam
*Assistant Examiner* — Ana Z Muresan
(74) *Attorney, Agent, or Firm* — Fishman & Associates, LLC.

(57) ABSTRACT

Provided is a process of preparing dichloropropanol, DCP. The process includes the step of: subjecting a three-carbon material to a first chlorination reaction with an aqueous hydrochloric acid solution in the presence of a carboxylic acid catalyst; adding the three-carbon material into the first mixture solution to undergo a second chlorination reaction and obtain a second mixture solution containing less than 13 wt % of hydrochloric acid; distilling the second mixture solution; and purifying the overhead product by oil-water separation to obtain DCP from the oil phase. By lowering the concentration of the hydrochloric acid contained in the mixture to be distilled, the DCP product can be straightly obtained via distillation and oil-water separation, thereby effectively simplifying the process of preparing DCP.

20 Claims, 4 Drawing Sheets

PROCESS FOR PREPARING DICHLOROPROPANOL

CROSS-REFERENCE TO RELATED APPLICATION

Pursuant to 35 U.S.C. §119(a), this application claims the benefit of the priority to Taiwan Patent Application No. 104142675 filed Dec. 18, 2015. The content of the prior application is incorporated herein by its entirety.

BACKGROUND

1. Field of the Disclosure

The present disclosure relates to a process of halohydrins, more particularly to a process of preparing dichloropropanol (DCP).

2. Description of the Prior Arts

DCP is an important precursor in the synthesis of epichlorohydrin (ECH). After reacting with alkaline substance, DCP is converted into ECH via dehydration and cyclization, so as to obtain the main raw material for the production of epoxy resin or chlorohydrin rubber.

Methods such as high-temperature chlorination of propylene, allyl acetate method, or chlorination of glycerin are conducted to prepare DCP nowadays. The first two methods employ chlorine to undergo an additional reaction of hypochlorous acid, thereby generating large amount of undesired chlorinated byproducts and leading to higher cost for the preparation of DCP.

Chinese Patent Publication No. 101429099 discloses the chlorination of glycerin. Depending on various chlorinating agents, the chlorination of glycerin can be achieved by two different approaches. One adopts gaseous hydrochloric acid, $HCl_{(g)}$, as the chlorinating agent to react with glycerin in the presence of acetic acid to produce DCP. Another approach adopts aqueous hydrochloric acid, $HCl_{(l)}$, as the chlorinating agent to overcome the problems of difficult accessibility or operation limits when using the gaseous hydrochloric acid. However, the second approach needs to feed concentrated aqueous hydrochloric acid in a concentration about 38% into the distillation column continuously, resulting in that larger amount of the hydrochloric acid is consumed in the preparation of DCP. Further, both approaches disclosed in the patent publication require two distillation columns, i.e., a reactive distillation column and a purifying distillation column, to complete the process. The patent publication does not disclose how to purify the overhead product from the reactive distillation column and how to recycle the aqueous hydrochloric acid.

Whatever methods used to prepare the DCP, dichloropropanol-hydrochloric acid solution including DCP, water, and hydrochloric acid are produced during the process. The presence of the triple azeotropic system causes the purification difficulties and complexities, resulting in that DCP and hydrochloric acid cannot be directly separated via the azeotropic distillation.

Chinese Patent Publication No. 101134714 discloses a solvent extraction for purification. Organic extraction solvent is mixed with the dichloropropanol-hydrochloric acid solution and then reacted in a specific extraction equipment to extract the DCP. Although the solvent extraction is capable of extracting 90% of DCP, the extraction cannot be performed as desired unless using the extraction solvent and additional extraction equipment. After the solvent extraction, further purification is also required to remove the extraction solvent from DCP. As a result, the approach in the prior art still costs high and causes lots of pollutions.

SUMMARY OF THE DISCLOSURE

In view that the conventional method fails to separate the dichloropropanol, aqueous hydrochloric acid, and water without the extraction solvent, an objective of the instant disclosure is to simplify the process and the system for preparing dichloropropanol, thereby straightly obtaining the desired product via distillation and oil-water separation after the chlorination reaction.

To achieve the foresaid objectives, the instant disclosure provides a process of preparing dichloropropanol including steps (a) to (d) in sequence. In step (a), a three-carbon material is reacted with an aqueous hydrochloric acid solution in the presence of a carboxylic acid catalyst for a first chlorination reaction, so as to obtain a first mixture solution. The three-carbon material comprises glycerin, glycerin ester, monochloropropanediol, monochloropropanediol ester or their combination. In step (b), another batch of the three-carbon material is added into the first mixture solution for a second chlorination reaction, so as to obtain a second mixture solution. Said second mixture solution contains hydrochloric acid in a concentration less than 13 wt %. In step (c), the second mixture solution is distilled to obtain an overhead product. In step (d), the overhead product is treated with an oil-water separation to separate the overhead product into an aqueous phase and an oil phase, and thus collect the desired dichloropropanol from the oil phase.

By means of reducing the concentration of hydrochloric acid contained in the second mixture solution to less than 13 wt %, the second mixture solution can be directly fed into the distillation column for distillation, and the overhead product can be purified by oil-water separation to simply collect the dichloropropanol from the bottom oil phase. Accordingly, the process of preparing dichloropropanol is useful to simplify the preparation of dichloropropanol and to complete the purification by distillation and oil-water separation.

In addition, the process of preparing dichloropropanol is beneficial to overcome the necessity of using extraction solvent or azeotropic agent to purify the dichloropropanol. It should be noted that one person skilled in the art still can use any appropriate extraction solvent or azeotropic agent in the instant process to prepare dichloropropanol if desired.

The concentration of the hydrochloric acid contained in the second mixture solution is preferably less than 11 wt %, more preferably less than 10 wt %, and further more preferably less than 9 wt %. Herein, the lower concentration of the hydrochloric acid contained in the second mixture solution is beneficial to increase the yield of the dichloropropanol.

In accordance with the instant disclosure, a molar ratio of the three-carbon material relative to the hydrochloric acid contained in the aqueous hydrochloric acid solution preferably ranges from 1:2 to 1:6, and more preferably ranges from 1:3 to 1:5. A molar ratio of the three-carbon material relative to the carboxylic acid catalyst preferably ranges from 1:0.1 to 1:1, more preferably ranges from 1:0.4 to 1:0.9, and further more preferably ranges from 1:0.4 to 1:0.7. With the molar ratio, the instant process is beneficial to improve the selectivity in the chlorination synthesis, and thus obtain larger amount of desired dichloropropanol.

Preferably, the carboxylic acid catalyst is a carboxylic acid having 1 to 8 carbon atoms, a carboxylic acid anhydride having 1 to 8 carbon atoms, or a carboxylic acid ester having 1 to 8 carbon atoms. The carboxylic acid catalyst applicable in the instant disclosure may be formic acid, acetic acid, propanoic acid, butanoic acid, hexanoic acid, 4-methylpentanoic acid, heptanoic acid, octanoic acid, succinic acid, adipic acid, terephthalic acid, or carboxylic acid anhydride from any one of the foresaid carboxylic acids, or carboxylic acid ester from any one of the foresaid carboxylic acids. More preferably, the carboxylic acid catalyst may be acetic acid. Further more preferably, the carboxylic acid catalyst may be glacial acetic acid.

Preferably, the aqueous hydrochloric acid as the chlorinating agent has a concentration equal to or more than 20 wt % and less than 40 wt %. More preferably, the aqueous hydrochloric acid has a concentration equal to or more than 30 wt % and equal to or less than 39 wt %.

Preferably, the first chlorination reaction in step (a) and the second chlorination reaction in step (b) are conducted at a temperature equal to or more than 80° C. and equal to or less than 150° C. More preferably, the first chlorination reaction and the second chlorination reaction are conducted at the temperature equal to or more than 100° C. and equal to or less than 130° C.

In accordance with the instant disclosure, the temperature of distillation can be modified depending on its pressure. In one case of the instant process, the distillation is performed under normal pressure, and the overhead temperature can be set at equal to or more than 95° C. and equal to or less than 115° C. In some cases, the distillation is performed under a negative pressure, for example, within 100 torr to 700 torr, and the overhead temperature can be set at equal to or more than 50° C. and equal to or less than 98° C. Preferably, the distillation is performed under 100 torr to 500 torr and at a temperature equal to or more than 51° C. and equal to or less than 90° C. When the distillation is performed under 100 torr to 300 torr, the overhead temperature can be set at equal to or more than 51° C. and equal to or less than 76° C.

Preferably, the three-carbon material may be a recycled crude glycerin, which is collected from a saline wastewater of the epichlorohydrin saponification process. For example, the saline wastewater before purification may contain more than 0 wt % and equal to or less than 5 wt % of glycerin, more than 0 wt % and equal to or less than 25 wt % of salts, from 60 wt % to 90 wt % of water, and more than 0 wt % and equal to or less than 10 wt % of impurities. After multiple purification steps, the amount of glycerin contained in the recycled crude glycerin can be effectively increased. For example, the purified recycled crude glycerin may contain about 70 wt % to 98 wt % of glycerin, 0 wt % to 15 wt % of water, 0 wt % to 1 wt % of salts, and 0 wt % to 15 wt % of impurities. Accordingly, the process of preparing dichloropropanol can recycle and reuse the saline wastewater from the epichlorohydrin saponification process to prepare dichloropropanol.

Preferably, the foresaid step (c) comprises step (c1): distilling the second mixture solution to obtain the overhead product and a bottom product; and step (c2): increasing the concentration of the hydrochloric acid contained in the bottom product to equal to or more than 20 wt % and less than 40 wt %, so as to obtain a recycled hydrochloric acid solution. The bottom product contains an unchlorinated three-carbon material (i.e., glycerin, glycerin ester, monochloropropanediol, or monochloropropanediol ester), the aqueous hydrochloric acid solution, and dichloropropanol. Said recycled hydrochloric acid solution can be employed to perform the chlorination reaction repeatedly, and followed by distillation and oil-water separation to collect another batch of dichloropropanol. Preferably, the foresaid step can increase the concentration of the hydrochloric acid contained in the bottom product to equal to or more than 21 wt % and equal to or less than 30 wt %, and more preferably, to equal to or more than 22 wt % and equal to or less than 27 wt %. In another embodiment of the instant disclosure, the concentration of the hydrochloric acid contained in the bottom product is equal to or more than 30 wt % and equal to or less than 39 wt %.

In some cases, step (c2) comprises the step of collecting the bottom product and the step of feeding a gaseous hydrochloric acid into the bottom product to increase the concentration of the hydrochloric acid contained in the bottom product to equal to or more than 20 wt % and less than 40 wt %, so as to obtain the recycled hydrochloric acid solution. Said recycled hydrochloric acid solution can be fed into the chlorination reactor to undergo the chlorination reaction in step (a) of the next repeated cycle. Herein, the concentration of hydrochloric acid can be increased by using a hydrochloric acid absorption column.

In some cases, step (c2) comprises the step of collecting the bottom product, the step of dehydrating the bottom product by using a purification column to obtain a dehydrated bottom product, and the step of feeding an aqueous hydrochloric acid supplement into the dehydrated bottom product to increase the concentration of the hydrochloric acid to equal to or more than 20 wt % and less than 40 wt %, so as to obtain the recycled hydrochloric acid solution. As stated above, the recycled hydrochloric acid solution also can be fed into the chlorination reactor to react with the three-carbon material and undergo the chlorination reaction in step (a) of the next repeated cycle. Herein, the concentration of hydrochloric acid also can be increased by using a hydrochloric acid purification column and supplying the aqueous hydrochloric acid solution.

Preferably, the aqueous phase obtained in step (d) can be fed back to the distillation column to perform a second distillation in the next repeated cycle.

Preferably, the process comprises repeating a cycle including steps (a) to (d) for at least one time, i.e., the desired product of dichloropropanol can be produced continuously through the repeated cycle operation.

More preferably, when repeating the cycle of steps (a) to (d), the aqueous hydrochloric acid solution employed in step (a) of the repeated cycle may be the recycled hydrochloric acid solution collected from step (c2) in the previous cycle. The concentration of the hydrochloric acid contained in the aqueous hydrochloric acid solution may be equal to or more than 20 wt % and less than 40 wt %.

More preferably, when repeating the cycle of steps (a) to (d), the repeated step (c) comprises distilling the second mixture solution and the aqueous phase collected from step (d) in the previous cycle, so as to obtain the overhead product. The aqueous hydrochloric acid solution can be fed into the distillation column and distilled with the other mixture solution to reuse the aqueous hydrochloric acid solution.

More preferably, in the repeated cycle of steps (a) to (d), the purification can be achieved through a single distillation in step (c) of each cycle. Accordingly, the process of preparing dichloropropanol is also useful to simplify the distillation step compared with the conventional process.

In accordance with the instant process, said dichloropropanol may be 1,3-dichloro-2-propanol, 2,3-dichloro-1-propanol, or their mixture.

Other objectives, advantages and novel features of the disclosure will become more apparent from the following detailed description when taken in conjunction with the accompanying drawings.

Figure 1:
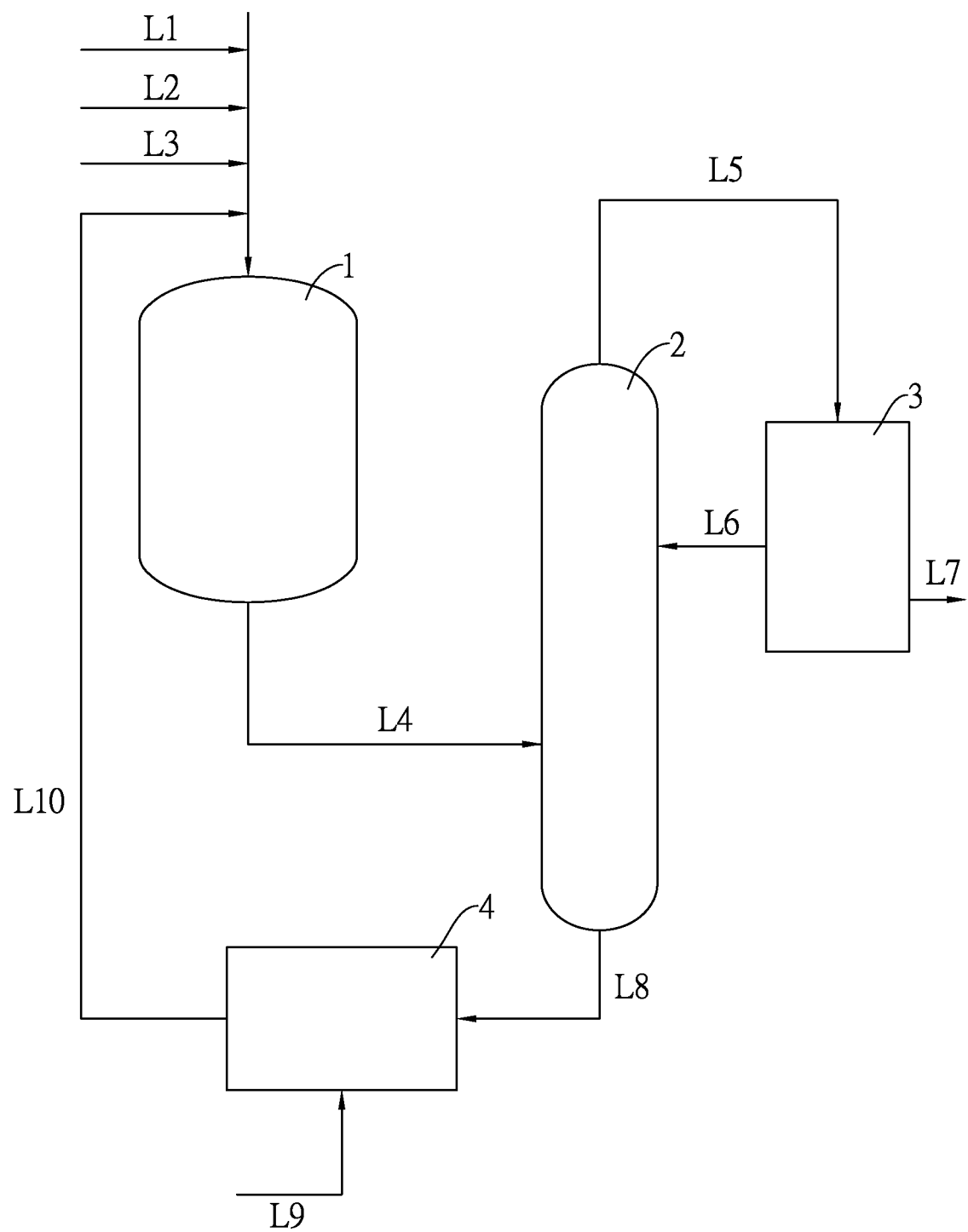
FIG. 1 is a flow diagram illustrating Preparation System Example 1.

It should be understood that the various aspects are not limited to the arrangements and instrumentality shown in the drawings.

DETAILED DESCRIPTION OF THE DISCLOSURE

Hereinafter, one skilled in the arts can easily realize the advantages and effects of the instant disclosure from the following examples. Therefore, it should be understood that the descriptions proposed herein are just preferable examples for the purpose of illustrations only, not intended to limit the scope of the disclosure. Various modifications and variations could be made in order to practice or apply the instant disclosure without departing from the spirit and scope of the disclosure.

Preparation System Example 1

One example of a system for preparing dichloropropanol applicable to the instant process is illustrated in FIG. 1. The system comprises a chlorination reactor 1, a distillation column 2, an oil-water separator 3, an hydrochloric acid absorption column 4, a three-carbon material inlet pipe L1, an aqueous hydrochloric acid inlet pipe L2, a catalyst inlet pipe L3, a chlorination outlet pipe L4, a condenser pipe L5, a reflux pipe L6, an oil outlet pipe L7, a bottom pipe L8, a gaseous hydrochloric acid inlet pipe L9, and a recycle pipe L10.

The three-carbon material inlet pipe L1, the aqueous hydrochloric acid inlet pipe L2, and the catalyst inlet pipe L3 are connected to the chlorination reactor 1, so as to feed the three-carbon material, aqueous hydrochloric acid solution and carboxylic acid catalyst into the chlorination reactor 1. Said chlorination reactor 1 is set at 100° C. to 150° C. and under 1 bar to 6 bar. The chlorination outlet pipe L4 is connected to the chlorination reactor 1, so as to release the chlorinated mixture from the chlorination reactor 1. In another embodiment, the system can set up with multiple chlorination reactors 1 as required.

The distillation column 2 is connected with the chlorination reactor 1 via the chlorination outlet pipe L4, such that the chlorinated mixture from the chlorination reactor 1 is supplied to the middle of the distillation column 2 via the chlorination outlet pipe L4. Herein, the chlorinated mixture supplied to the distillation column 2 contains hydrochloric acid in the concentration less than 13 wt %.

The oil-water separator 3 is connected with an overhead outlet of the distillation column 2 via the condenser pipe L5, such that the oil-water separator 3 is supplied with the overhead product coming from the distillation column 2 via the condenser pipe L5. Further, the reflux pipe L6 is set between the oil-water separator 3 and the distillation column 2 for refluxing the aqueous phase of the oil-water separator 3 into the distillation column 2. The oil outlet pipe L7 is also connected to the oil-water separator 3 for releasing the dichloropropanol contained in the oil phase.

The hydrochloric acid absorption column 4 is connected with a bottom outlet of the distillation column 2 via the bottom pipe L8, such that the hydrochloric acid absorption column 4 is supplied with the bottom product coming from the distillation column 2 via the bottom pipe L8.

The gaseous hydrochloric acid inlet pipe L9 is connected to the hydrochloric acid absorption column 4, so as to supply the gaseous hydrochloric acid into the hydrochloric acid absorption column 4 and thereby increase the concentration of the hydrochloric acid of the mixture in the hydrochloric acid absorption column 4. Further, the recycle pipe L10 is set between the hydrochloric acid absorption column 4 and the chlorination reactor 1, such that the recycled hydrochloric acid solution with more hydrochloric acid from the hydrochloric acid absorption column 4 can be fed into the chlorination reactor 1 for the subsequent chlorination reaction.

Preparation System Example 2

Figure 2:
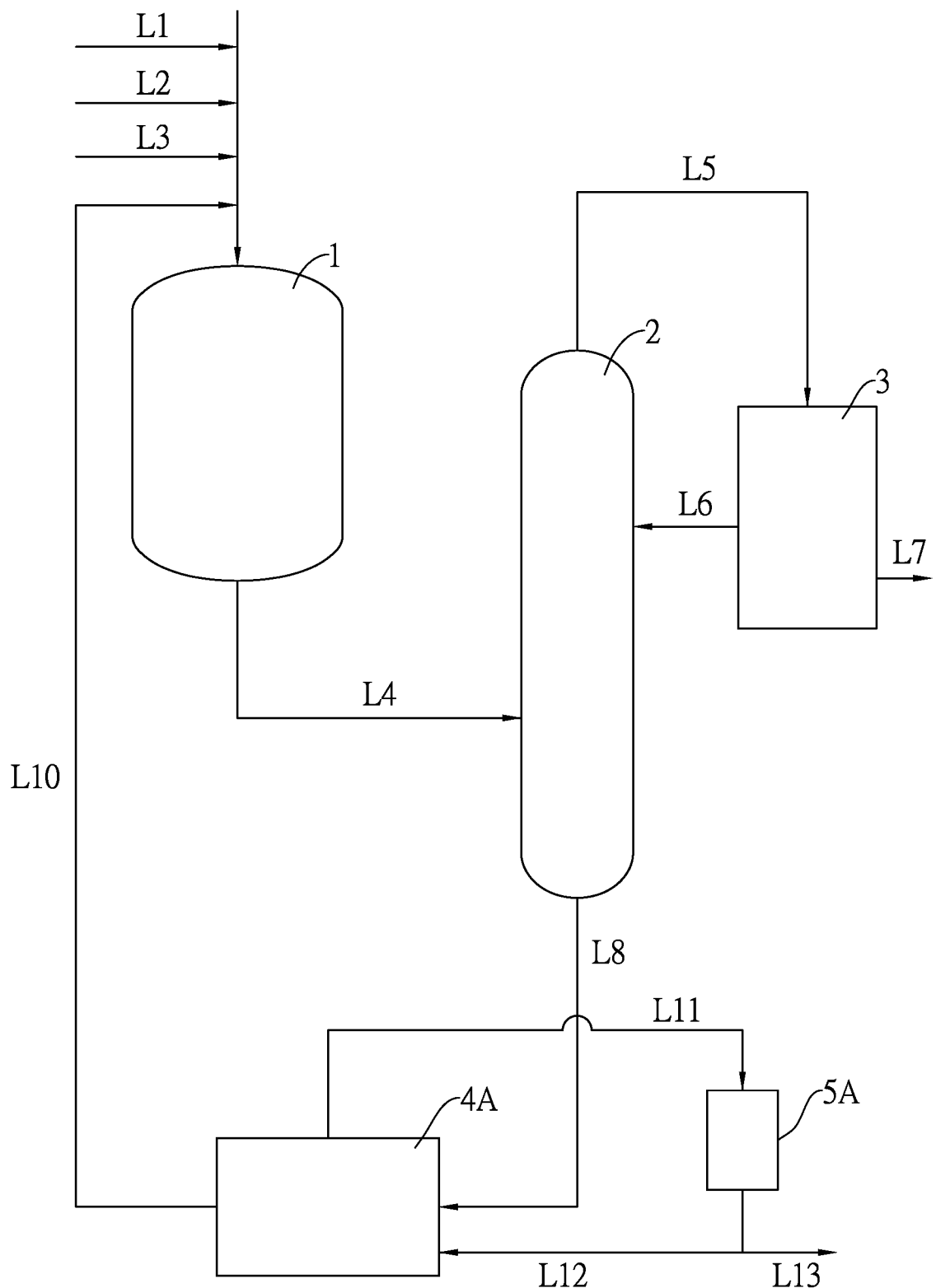
FIG. 2 is a flow diagram illustrating Preparation System Example 2.

Another example of a system for preparing dichloropropanol applicable to the instant process is illustrated in FIG. 2. The system comprises a chlorination reactor 1, a distillation column 2, an oil-water separator 3, a three-carbon material inlet pipe L1, an aqueous hydrochloric acid inlet pipe L2, a catalyst inlet pipe L3, a chlorination outlet pipe L4, a condenser pipe L5, a reflux pipe L6, an oil outlet pipe L7, a bottom pipe L8, and a recycle pipe L10, which are similar with those as stated above in the first preparation system.

The differences between the first and the second preparation systems are that the hydrochloric acid absorption column is replaced by the hydrochloric acid purification column 4A and the second preparation system further comprises a condensate collection tank 5A, a connection pipe L11, a fluid recycling pipe L12, and a drain pipe L13.

In the second preparation system, the hydrochloric acid purification column 4A is connected with a bottom outlet of the distillation column 2 via the bottom pipe L8, such that the hydrochloric acid purification column 4A is supplied with the bottom product coming from the distillation column 2 via the bottom pipe L8. The top of the hydrochloric acid purification column 4A is connected with the condensate collection tank 5A via the connection pipe L11. The condensate collection tank 5A is installed with the fluid recycling pipe L12 and the drain pipe L13, such that the dehydrated mixture can be fed back to the hydrochloric acid purification column 4A via the fluid recycling pipe L12 and the remaining solution can be released through the drain pipe L13. Further, the recycle pipe L10 is set between the hydrochloric acid purification column 4A and the chlorination reactor 1, so as to feed the dehydrated hydrochloric acid solution into the chlorination reactor 1 for the subsequent chlorination reaction.

Process of Preparing Dichloropropanol

EXAMPLE 1

Figure 3:
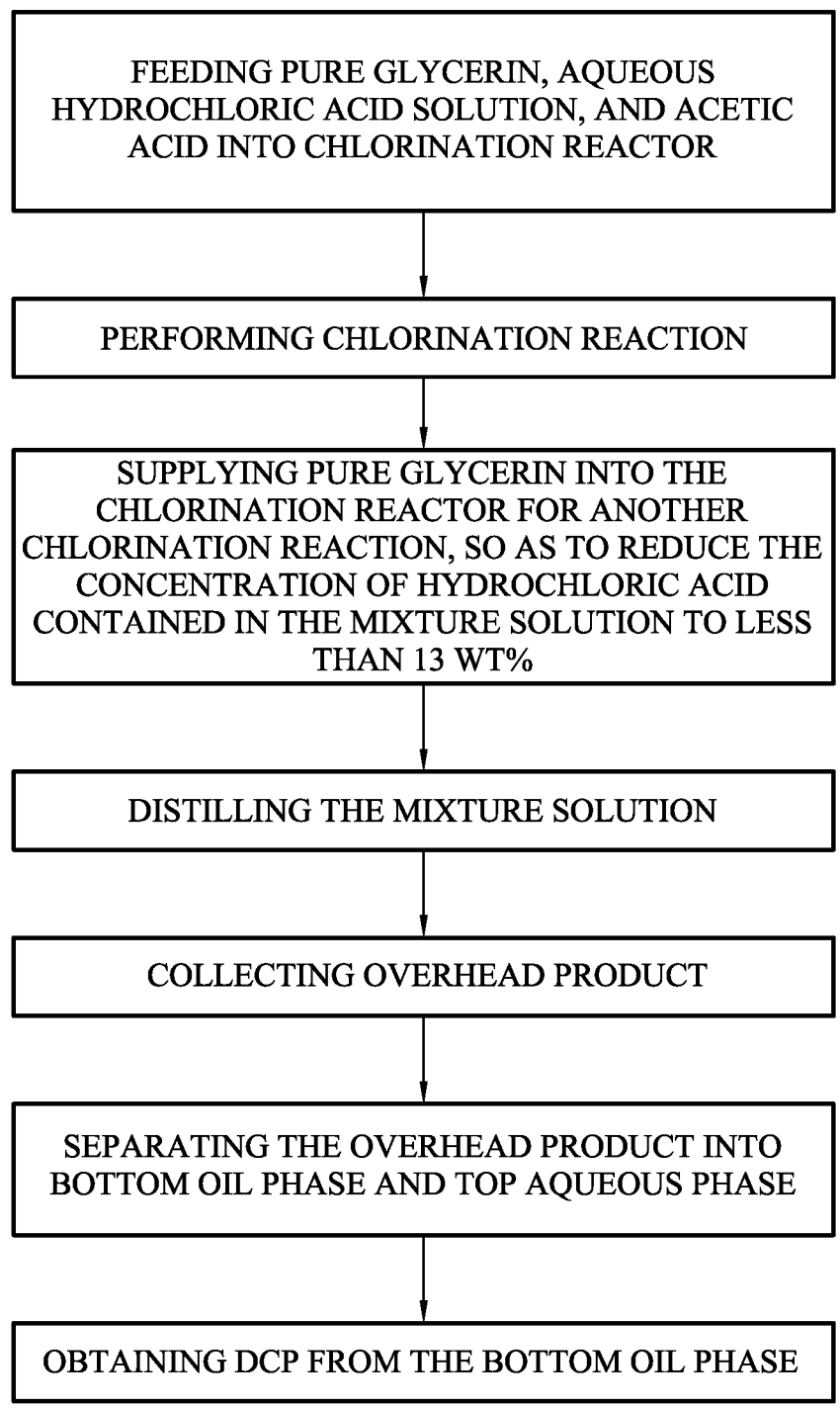
FIG. 3 is a block diagram illustrating an embodiment of the instant process.

Hereinafter, the process of preparing dichloropropanol was conducted by using the first preparation system as shown in FIG. 1 and according to the steps as shown in FIG. 3.

First, in step (a), the chlorination reactor 1 was supplied with pure glycerin via the three-carbon material inlet pipe L1, 36.8 wt % of aqueous hydrochloric acid solution via the aqueous hydrochloric acid inlet pipe L2, and acetic acid via the catalyst inlet pipe L3, and thermostated at 125° C. for 2 hours to perform a first chlorination reaction. Then a first mixture solution was obtained. The molar ratio of pure glycerin, hydrochloric acid contained in the aqueous hydrochloric acid solution, and acetic acid was 1.0:4.0:0.6. Based on the titration result of the first mixture solution, the concentration of hydrochloric acid contained in the first mixture solution was 17.4 wt %, and the conversion rate of glycerin was about 91.4%.

Subsequently, in step (b), the chlorination reactor 1 was supplied again with equimolar amount of pure glycerin via the three-carbon material inlet pipe L1, and thermostated at 125° C. for 2 hours to perform a second chlorination reaction. When the second chlorination reaction was completed, a second mixture solution was obtained. Based on the titration result of the second mixture solution, the concentration of hydrochloric acid contained in the second mixture solution was reduced to 11.2 wt %. The consumption of glycerin was 150.6 grams, and 75.4 grams of dichloropropanol with a chlorination yield of 35.7% was produced. The chlorination yield (%) was calculated by dividing the number of moles of produced dichloropropanol by the number of consumption moles of glycerin and multiplying 100%.

Then, in step (c), the second mixture solution from the chlorination reactor 1 was fed into the distillation column 2 via the chlorination outlet pipe L4, and then distilled in the distillation column 2 with an overhead temperature at 101° C. and under normal pressure. After that, the overhead product from the distillation column 2 was fed into the oil-water separator 3 via the condenser pipe L5.

Finally, in step (d), the overhead product was separated into a top aqueous phase and a bottom oil phase containing 72.3 wt % of dichloropropanol. The top aqueous phase was refluxed into the distillation column 2 via the reflux pipe L6, and the bottom oil phase was released from the bottom of the oil-water separator 3 via the oil outlet pipe L7. Accordingly, 24.9 grams of dichloropropanol with a distillation yield of 33.0% was obtained. Said distillation yield (%) was calculated by dividing the amount of dichloropropanol contained in the bottom oil phase by the amount of dichloropropanol contained in the feeding to be distilled and multiplying 100%.

EXAMPLE 2

Figure 4:
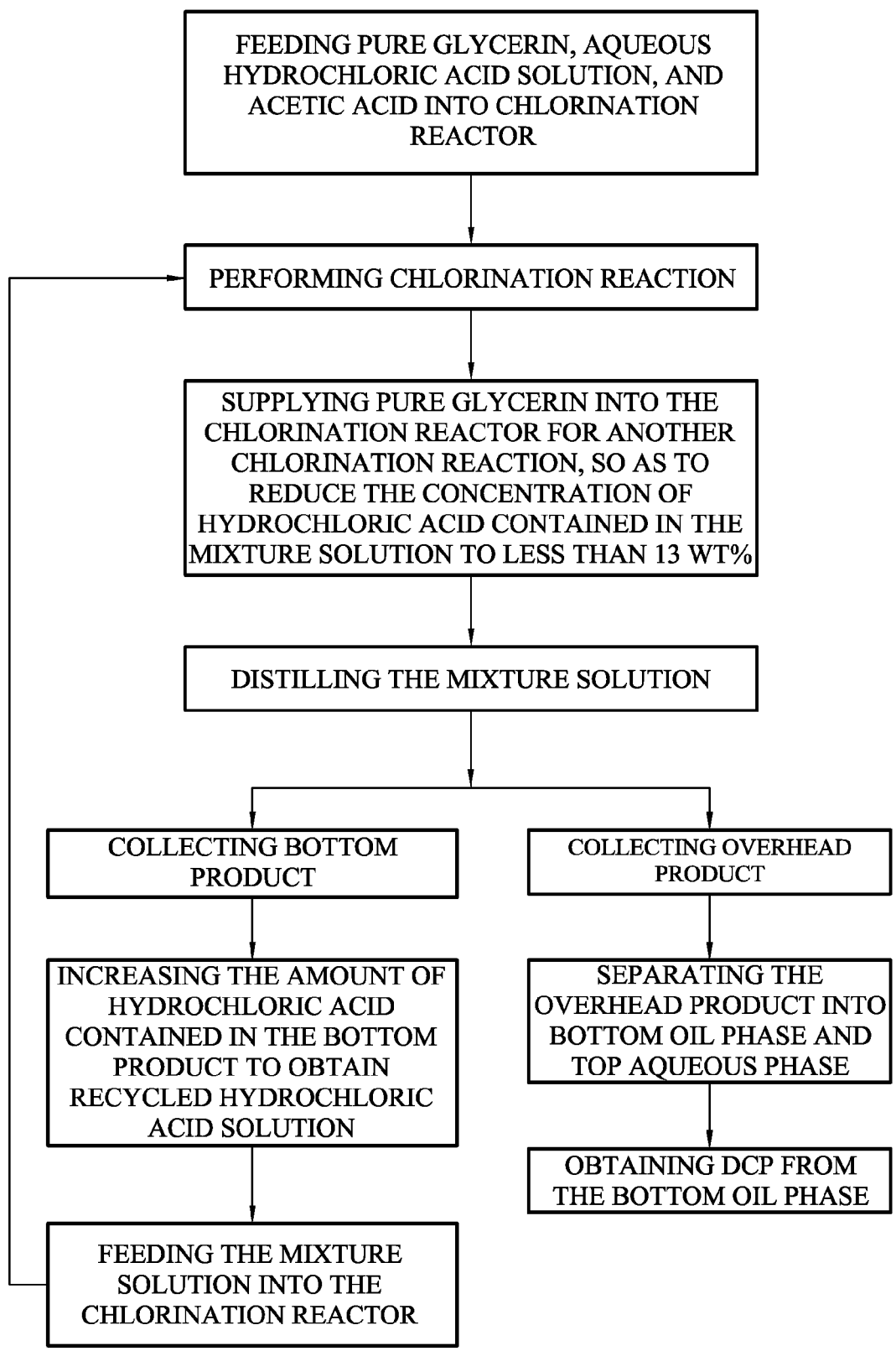
FIG. 4 is a block diagram illustrating another embodiment of the instant process.

With reference to FIGS. 1 and 4, the process of preparing dichloropropanol was conducted as the process similar to that of Example 1. The differences between Examples 1 and 2 were that the process of Example 2 further repeated the following steps.

The bottom product collected from the distillation column 2 in the process of Example 1 was fed into the hydrochloric acid absorption column 4 via the bottom pipe L8. The bottom product contained about 8.0 wt % of glycerin, about 18.2 wt % of monochloropropanediol, about 7.0 wt % of dichloropropanol, about 10.5 wt % of aqueous hydrochloric acid solution, about 4.5 wt % of acetic acid, and 48.2 wt % of water.

After that, the hydrochloric acid absorption column 4 was supplied with gaseous hydrochloric acid via the gaseous hydrochloric acid inlet pipe L9, so as to increase the concentration of hydrochloric acid contained in the bottom product to 23.4 wt % and to obtain a recycled hydrochloric acid solution.

Said recycled hydrochloric acid solution could be used as a reactant of the chlorination reaction. In step (a) of the next repeated cycle, the chlorination reactor 1 was supplied with the recycled hydrochloric acid solution via the recycle pipe L10, and then thermostated at 125° C. for 1 hour to perform a repeated first chlorination reaction and obtain a third mixture solution.

In step (b) of the next repeated cycle, the chlorination reactor 1 was further supplied with 110.4 grams of pure glycerin and thermostated at 125° C. for 2 hours to perform a repeated chlorination reaction. Then a fourth mixture solution was obtained. Based on the titration result of the fourth mixture solution, the concentration of hydrochloric acid in the fourth mixture solution was reduced to 9.1 wt %. The consumption of glycerin was 105.1 grams, and 92.8 grams of dichloropropanol with a chlorination yield of 63.0% was produced.

After that, in the repeated step (c), the fourth mixture solution containing 120.2 grams of dichloropropanol was fed into the distillation column 2, and the fourth mixture solution was distilled with the aqueous phase refluxed in step (d) of the previous cycle, i.e., the aqueous phase refluxed into the distillation column 2 in step (d) of Example 1, in the distillation column 2 with an overhead temperature at 102° C. and under normal pressure. The overhead product from the distillation column 2 was then fed into the oil-water separator 3 via the condenser pipe L5.

The oil-water separation as described in Example 1 was conducted again, and 62.4 grams of dichloropropanol with a distillation yield of 51.9% was finally obtained from the bottom oil phase.

EXAMPLE 3

Before the chlorination reaction, a saline wastewater from epichlorohydrin saponification was collected, and concentrated and purified as described below to obtain the glycerin material for chlorination reaction. The desired dichloropropanol was obtained by the first preparation system through the twice chlorination reactions, distillation and oil-water separation.

The details of the process of preparing dichloropropanol from the saline wastewater was conducted as follows:

First, 5000 grams of saline wastewater from epichlorohydrin saponification was concentrated through multiple stages to dehydrate 2917.8 grams of water. The concentrated solution was filtered to remove 1072.0 grams of salts, finally collecting 1010.2 grams of recycled crude glycerin. The recycled crude glycerin contained about 51.9 wt % of glycerin, about 11.7 wt % of water, about 34.3 wt % of impurities, and about 2.1 wt % of salts.

Subsequently, 1010.2 grams of recycled crude glycerin was distilled under negative pressure to remove most salts and impurities, and thereby collecting 464.3 grams of glycerin with a purity of 84.6% from the overhead of the distillation column. Said recycled crude glycerin could be used as the three-carbon material for the subsequent chlorination reaction.

After that, in step (a), 110 grams of the recycled crude glycerin collected from the foresaid process was mixed with hydrochloric acid and acetic acid at a molar ratio of 1.0:3.0:0.6. The chlorination reactor 1 was supplied with the recycled crude glycerin via the three-carbon material inlet pipe L1, 35.3 wt % of aqueous hydrochloric acid solution via the aqueous hydrochloric acid inlet pipe L2, and acetic acid via the catalyst inlet pipe L3, and thermostated at 125° C. for 2 hours to perform a first chlorination reaction. When the first chlorination reaction was completed, a first mixture solution was obtained. Based on the titration result of the first mixture solution, the concentration of hydrochloric acid contained in the first mixture solution was 15.6 wt %, and the conversion rate of glycerin was about 91.6%.

Then, in step (b), the chlorination reactor 1 was further supplied with equimolar amount of the recycled crude glycerin via the three-carbon material inlet pipe L1, and thermostated at 120° C. for 2 hours to perform a second chlorination reaction. A second mixture solution was obtained. Based on the titration result of the second mixture solution, the concentration of hydrochloric acid contained in the second mixture solution was reduced to 9.6 wt %. The consumption of glycerin was 135.1 grams, and 39.2 grams of dichloropropanol with a chlorination yield of 20.7% was produced.

Next, in step (c), the second mixture solution from the chlorination reactor 1 was fed into the distillation column 2 via the chlorination outlet pipe L4, and then distilled in the distillation column 2 with an overhead temperature at 76° C. and under a negative pressure of 260 torr, so as to purify the second mixture solution. After distillation, the overhead product was fed into the oil-water separator 3 via the condenser pipe L5 to be separated into two phases. Finally, in step (d), the overhead product was separated into a top aqueous phase and a bottom oil phase containing 80.4 wt % of dichloropropanol. The top aqueous phase was refluxed into the distillation column 2 via the reflux pipe L6, and the bottom oil phase was released from the bottom of the oil-water separator 3 via the oil outlet pipe L7 to collect 27.6 grams of dichloropropanol. Herein, the distillation yield was 70.4%.

EXAMPLE 4

The process of preparing dichloropropanol was conducted as the process similar to that of Example 3. The differences between Examples 3 and 4 were that the process of Example 4 further repeated the following steps.

After the first cycle of the process as described in Example 3, the bottom product collected from the distillation column 2 as described in Example 3 was fed into the hydrochloric acid absorption column 4 via the bottom pipe L8. The bottom product contained about 9.4 wt % of glycerin, about 19.2 wt % of monochloropropanediol, about 2.3 wt % of dichloropropanol, about 10.3 wt % of hydrochloric acid, about 4.6 wt % of acetic acid, and about 44.6 wt % of water.

Then the hydrochloric acid absorption column 4 was supplied with gaseous hydrochloric acid via the gaseous hydrochloric acid inlet pipe L9, so as to increase the concentration of hydrochloric acid contained in the bottom product to 22.8 wt % and to obtain a recycled hydrochloric acid solution.

In step (a) of the next repeated cycle, the chlorination reactor 1 was supplied with the recycled hydrochloric acid solution via the recycle pipe L10, and then thermostated at 120° C. for 2 hours to perform a repeated first chlorination reaction and obtain a third mixture solution.

In step (b) of the next repeated cycle, the chlorination reactor 1 was further supplied with 108.7 grams of recycled crude glycerin with a purity of 85.5%, thermostated at the same temperature for 2 hours to perform a repeated chlorination reaction, and then obtained a fourth mixture solution. Based on the titration result of the fourth mixture solution, the concentration of hydrochloric acid in the fourth mixture solution was reduced to 8.4 wt %. The consumption of glycerin was 94.4 grams, and 108.3 grams of dichloropropanol with a chlorination yield of 81.8% was produced.

After that, in step (c) of the next repeated cycle, the fourth mixture solution containing 111.4 grams of dichloropropanol was fed into the distillation column 2, and the fourth mixture solution was distilled with the aqueous phase refluxed in step (d) of the previous cycle, i.e., the aqueous phase refluxed into the distillation column 2 in step (d) of Example 3, in the distillation column 2 under a negative pressure. The overhead product from the distillation column 2 was then fed into the oil-water separator 3 via the condenser pipe L5.

Finally, the oil-water separation as described in Example 3 was repeated again, and thus 66.2 grams of dichloropropanol with a distillation yield of 59.4% was obtained from the bottom oil phase.

EXAMPLE 5

The process of preparing dichloropropanol was conducted by using the second preparation system as shown in FIG. 2 and according to the steps as described below.

The collected bottom product contained about 9.4 wt % of glycerin, about 2.2 wt % of dichloropropanol, about 19.2 wt % of monochloropropanediol, about 10.3 wt % of hydrochloric acid, about 4.6 wt % of acetic acid, and about 44.6 wt % of water. The collected bottom product was fed into the hydrochloric acid purification column 4A via the bottom pipe L8. With the condensate collection tank 5A, the mixture coming from the top of the hydrochloric acid purification column 4A was dehydrated to contain only 13.2 wt % of water, and thus obtained a concentrated and dehydrated hydrochloric acid solution. The water could be released through the drain pipe L13.

Subsequently, the dehydrated hydrochloric acid solution was fed back to the chlorination column 1 via the recycle pipe L10. Also, the chlorination reactor 1 was supplied with 36.8 wt % of aqueous hydrochloric acid solution (containing 3.5 moles of hydrochloric acid) via the aqueous hydrochloric acid inlet pipe L2 to increase the concentration of hydrochloric acid to 24.6 wt %. Then 0.6 moles of acetic acid was fed into the chlorination column 1 via the catalyst inlet pipe L3. The third chlorination reaction was performed at 130° C. for 1 hour to obtain a third mixture solution.

After that, the chlorination reactor 1 was supplied again with 1 mole of the crude glycerin (with a purity of 85%) via the three-carbon material inlet pipe L1, and thermostated at 130° C. for 1 hour to perform a fourth chlorination reaction, and obtain a fourth mixture solution. Based on the titration result of the fourth mixture solution, the concentration of hydrochloric acid contained in the fourth mixture solution was reduced to 10.0 wt %. The consumption of glycerin was 101.8 grams, and 96.3 grams of dichloropropanol with a chlorination yield of 67.5% was produced.

Finally, the distillation and oil-water separation as described in Example 3 was repeated again, and thus 51.4 grams of dichloropropanol with a distillation yield of 53.5% was obtained from the bottom oil phase. Herein the feeding charged into the distillation column 2 contained 96.0 grams of dichloropropanol.

By means of the repeated cycle operation, the process of preparing dichloropropanol of Example 5 can fully omit the use of gaseous hydrochloric acid and improve the process safety.

COMPARATIVE EXAMPLE 1

The three-carbon material used in the Comparative Example was a recycled crude glycerin with a purity of 67.4 wt %. The recycled crude glycerin, hydrochloric acid, and acetic acid at a molar ratio of 1.0:5.0:0.7, were thermostated at 130° C. for 1.5 hours for a first chlorination reaction, and then a first mixture solution was obtained. Based on the titration result of the first mixture solution, the concentration of hydrochloric acid contained in the first mixture solution was 18.8 wt %. The conversion rate of glycerin was 97.3 wt %, the consumption of glycerin was 65.7 grams, and 65.1 grams of dichloropropanol with a chlorination yield of 70.7% was produced.

Then the first mixture solution was directly fed into the distillation column 2 from the chlorination reactor 1 via the chlorination outlet pipe L4, and then distilled in the distillation column 2 with an overhead temperature at 106° C. and under a normal pressure. After titration, the overhead product, i.e, dichloropropanol-hydrochloric acid solution containing 55.7 grams of dichloropropanol, was fed into the oil-water separator 3 via the condenser pipe L5 to be separated into two phases. However, no oil-water separation could be observed in the oil-water separator 3 after feeding the overhead product into the oil-water separator 3. Said bottom product contained about 15.6 wt % of aqueous hydrochloric acid solution, about 64.4 wt % of water, about 5.0 wt % of acetic acid, and about 3.5 wt % of dichloropropanol, and also contained about 4.2 wt % of monochloropropanol and impurities.

It can be seen that the process of Comparative Example 1 fails to straightly collect the desired product through a single distillation step and oil-water separation step. Other complicated purification steps are needed for the preparation of dichloropropanol.

Discussion of the Results

Based on the results of Examples 1 to 5, the instant process, which employs aqueous hydrochloric acid solution as chlorinating agent and controls the concentration of the mixture solution feeding into the distillation column, i.e., the foresaid second or the fourth mixture solution, to be less than 13 wt %, can simply obtain the desired dichloropropanol through single distillation and oil-water separation steps. Further, the aqueous phase obtained from the oil-water separation is mainly composed of aqueous hydrochloric acid solution, thus it is feasible to reflux the aqueous phase back to the distillation column to reuse the aqueous hydrochloric acid solution.

From the comparison results of Examples 1 to 5 and Comparative Example 1, the process of Comparative Example 1 does not control the concentration of the mixture solution feeding into the distillation column, such that the overhead product collected after the distillation cannot be separated into two different phases for the purification and other complicated purification steps are required to obtain the desired product of dichloropropanol. Further, the process of Comparative Example 1 hardly recycles and reuses the aqueous hydrochloric acid solution from the overhead product. Accordingly, the problems of process complexity, high cost, and excessive amount of acid waste still cannot be overcome by the process of Comparative Example 1.

From the results of Examples 3 and 4, the three-carbon material for chlorination reaction can be obtained from the saline wastewater of saponification process from the epichlorohydrin factory. After appropriate concentration and purification steps, the saline wastewater can be purified into the recycled crude glycerin, which is suitable to be a three-carbon material for chlorination step. Dichloropropanol can be obtained through the chlorination, distillation, and oil-water separation steps. Thus, the process of Examples 3 and 4 not only improves the utilization of glycerin contained in the saline wastewater, but also reduces the pollution of liquid waste and its pollution treatment cost.

From the results of Examples 2, 4, and 5, the unreacted glycerin, glycerin ester, monochloropropanediol, monochloropropanediol ester remaining in the bottom product of the distillation column also can be employed as the three-carbon material and be fed back to the chlorination reactor for another chlorination reaction, such that the utilization of glycerin and intermediates and chlorination yield of dichloropropanol are largely increased. With the repeated cycle operation, the instant process can reuse the aqueous hydrochloric acid solution and acetic acid to reduce the overall produced acid waste. Besides, the foresaid cycle is not limited to be executed only twice in the process. The instant process can be executed with multiple continuous cycles, each including the steps as stated in above Examples 2, 4, and 5, if desired.

Compared with the conventional process, the instant process can obtain the desired dichloropropanol from the bottom oil phase after the completion of chlorination, followed by distillation and oil-water separation. Accordingly, the instant process is effective to simplify the process, reduce the production cost, and reduce the amount of the produced acid waste. Meanwhile, compared with the conventional preparation system, the system used in the instant disclosure involves less equipment and is more suitable to execute repeated cycle operation, thereby being beneficial to largely reduce the amount of wastewater and acid waste and to avoid the pollution produced by extraction solvent.

Even though numerous characteristics and advantages of the instant disclosure have been set forth in the foregoing description, together with details of the structure and features of the disclosure, the disclosure is illustrative only. Changes may be made in the details, especially in matters of shape, size, and arrangement of parts within the principles of the disclosure to the full extent indicated by the broad general meaning of the terms in which the appended claims are expressed.

What is claimed is:

1. A process of preparing dichloropropanol, comprising steps of:
    step (a): subjecting a three-carbon material to a first chlorination reaction with an aqueous hydrochloric acid solution in the presence of a carboxylic acid catalyst, to obtain a first mixture solution, the three-carbon material comprising glycerin, glycerin ester, monochloropropanediol, monochloropropanediol ester or their combination;
    step (b): adding the three-carbon material into the first mixture solution to undergo a second chlorination reaction, to obtain a second mixture solution, the second mixture solution containing hydrochloric acid in a concentration less than 13 wt %;
    step (c): distilling the second mixture solution to obtain an overhead product; and
    step (d): separating the overhead product into an oil phase and an aqueous phase, to collect the dichloropropanol from the oil phase.

2. The process as claimed in claim 1, wherein a molar ratio of the three-carbon material relative to the hydrochloric acid contained in the aqueous hydrochloric acid solution ranges from 1:2 to 1:6.

3. The process as claimed in claim 1, wherein a molar ratio of the three-carbon material relative to the carboxylic acid catalyst ranges from 1:0.1 to 1:1, and the carboxylic acid catalyst is a carboxylic acid having 1 to 8 carbon atoms, a carboxylic acid anhydride having 1 to 8 carbon atoms, or a carboxylic acid ester having 1 to 8 carbon atoms.

4. The process as claimed in claim 3, wherein the carboxylic acid catalyst is acetic acid.

5. The process as claimed in claim 1, wherein a concentration of the aqueous hydrochloric acid solution is equal to or more than 20 wt % and less than 40 wt %.

6. The process as claimed in claim 1, wherein the first chlorination reaction in step (a) and the second chlorination reaction in step (b) are conducted at a temperature equal to or more than 80° C. and equal to or less than 150° C.

7. The process as claimed in claim 1, wherein the concentration of the hydrochloric acid contained in the second mixture solution is less than 11 wt %.

8. The process as claimed in claim 7, wherein the concentration of the hydrochloric acid contained in the second mixture solution is less than 10 wt %.

9. The process as claimed in claim 1, wherein the process comprises repeating a cycle of steps (a) to (d) for at least one time.

10. The process as claimed in claim 1, wherein the three-carbon material is a recycled crude glycerin, and the recycled crude glycerin is collected from a saline wastewater from epichlorohydrin saponification.

11. The process as claimed in claim 1, wherein step (c) comprises:
    step (c1): distilling the second mixture solution to obtain the overhead product and a bottom product, the bottom product containing an unchlorinated three-carbon material, the aqueous hydrochloric acid solution, and dichloropropanol; and
    step (c2): increasing a concentration of the hydrochloric acid contained in the bottom product to equal to or more than 20 wt % and less than 40 wt %, to obtain a recycled hydrochloric acid solution.

12. The process as claimed in claim 11, wherein step (c2) comprises:
    collecting the bottom product; and
    feeding a gaseous hydrochloric acid into the bottom product to increase the concentration of the hydrochloric acid contained in the bottom product to equal to or more than 20 wt % and less than 40 wt %, to obtain the recycled hydrochloric acid solution.

13. The process as claimed in claim 11, wherein step (c2) comprises:
    collecting the bottom product;
    dehydrating the bottom product to obtain a dehydrated bottom product; and
    feeding an aqueous hydrochloric acid supplement into the dehydrated bottom product to increase the concentration of the hydrochloric acid to equal to or more than 20 wt % and less than 40 wt %, to obtain the recycled hydrochloric acid solution.

14. The process as claimed in claim 11, wherein the process comprises repeating a cycle of steps (a) to (d) for at least one time, and the aqueous hydrochloric acid solution used in step (a) of the repeated cycle is the recycled hydrochloric acid solution.

15. The process as claimed in claim 12, wherein the process comprises repeating a cycle of steps (a) to (d) for at least one time, and the aqueous hydrochloric acid solution used in step (a) of the repeated cycle is the recycled hydrochloric acid solution.

16. The process as claimed in claim 13, wherein the process comprises repeating a cycle of steps (a) to (d) for at least one time, and the aqueous hydrochloric acid solution used in step (a) of the repeated cycle is the recycled hydrochloric acid solution.

17. The process as claimed in claim 1, wherein the process comprises repeating a cycle of steps (a) to (d) for at least one time, and step (c) of the repeated cycle comprises distilling the second mixture solution and the aqueous phase to obtain the overhead product.

18. The process as claimed in claim 14, wherein step (c) of the repeated cycle comprises distilling the second mixture solution and the aqueous phase to obtain the overhead product.

19. The process as claimed in claim 15, wherein step (c) of the repeated cycle comprises distilling the second mixture solution and the aqueous phase to obtain the overhead product.

20. The process as claimed in claim 16, wherein step (c) of the repeated cycle comprises distilling the second mixture solution and the aqueous phase to obtain the overhead product.

* * * * *